United States Patent [19]

Maroulis et al.

[11] Patent Number: 5,006,315
[45] Date of Patent: Apr. 9, 1991

[54] AUTOMATED PREPARATIVE GAS CHROMATOGRAPH

[75] Inventors: Peter J. Maroulis, Allentown; Patrick J. Clark, Palmerton; Victoria J. Morris, Macungie; Robert A. Byerley, Lehighton, all of Pa.; John Booker, Austin, Tex.

[73] Assignee: Air Products and Chemicals, Inc., Allentown, Pa.

[21] Appl. No.: 515,295

[22] Filed: Apr. 27, 1990

Related U.S. Application Data

[62] Division of Ser. No. 160,541, Feb. 25, 1988.

[51] Int. Cl.[5] .......................................... G01N 30/02
[52] U.S. Cl. ...................................... 422/89; 436/161; 73/23.35; 55/386
[58] Field of Search .................. 422/89, 99, 240, 101, 422/102; 436/161; 73/23.35; 55/386, 67, 197

[56] References Cited

U.S. PATENT DOCUMENTS

| | | |
|---|---|---|
| 2,076,903 | 4/1937 | Levitt ................................ 422/101 X |
| 3,267,646 | 8/1966 | Kauss et al. ........................... 55/197 |
| 3,390,513 | 7/1968 | Jeutzsch et al. ...................... 55/197 |
| 3,408,793 | 11/1968 | Frazer ................................... 55/197 |
| 3,996,008 | 12/1976 | Fine et al. ............................. 422/89 |
| 4,756,725 | 7/1988 | Badey et al. ....................... 422/101 X |
| 4,863,871 | 9/1989 | Munari et al. ....................... 422/89 X |

OTHER PUBLICATIONS

Roeraade, J. and Enzell, C. R., "Preparative Gas Chromatography with Glass Capillary Columns", J. of High Resolution Chromatography & Chromatography Communications, (Mar. 1979), pp. 123-132.

Primary Examiner—Robert J. Warden
Assistant Examiner—Lynn M. Kummert
Attorney, Agent, or Firm—Richard A. Dannells, Jr.; James C. Simmons; William F. Marsh

[57] ABSTRACT

A preparative-scale gas chromatographic system has conduits and valves adapted for analysis and collection of low volatility effluent. An injection site is provided for alternately supplying liquid solvent for removing condensed effluent from the system when the flow of effluent is terminated. Conduits are joined within the thermal conductivity detector of the system to prevent condensation at the joint. Conduits are provided with copper jackets which are coupled to sources of thermal energy to prevent condensation within the conduits. A trap filter provides backpressure in the collection system wherein recovery of condensed effluent in the filter is facilitated by the smooth surface of the filter.

3 Claims, 12 Drawing Sheets

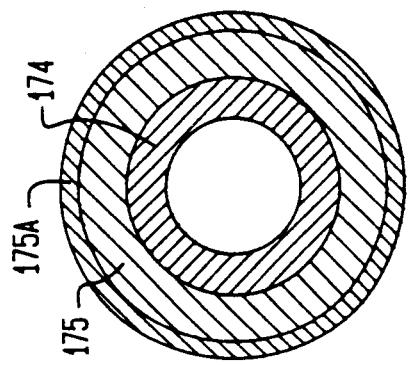
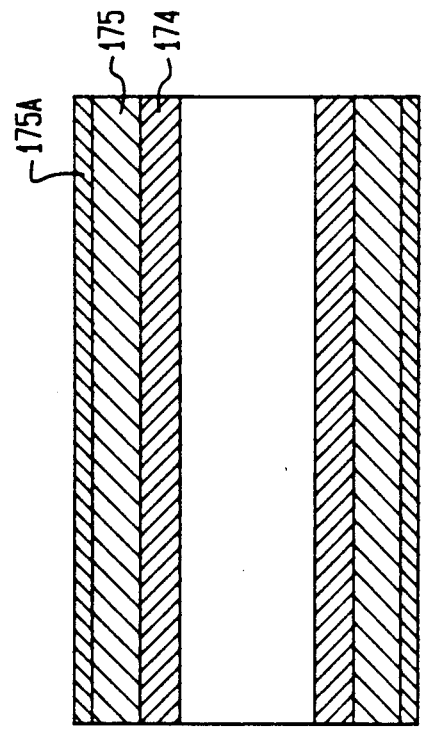

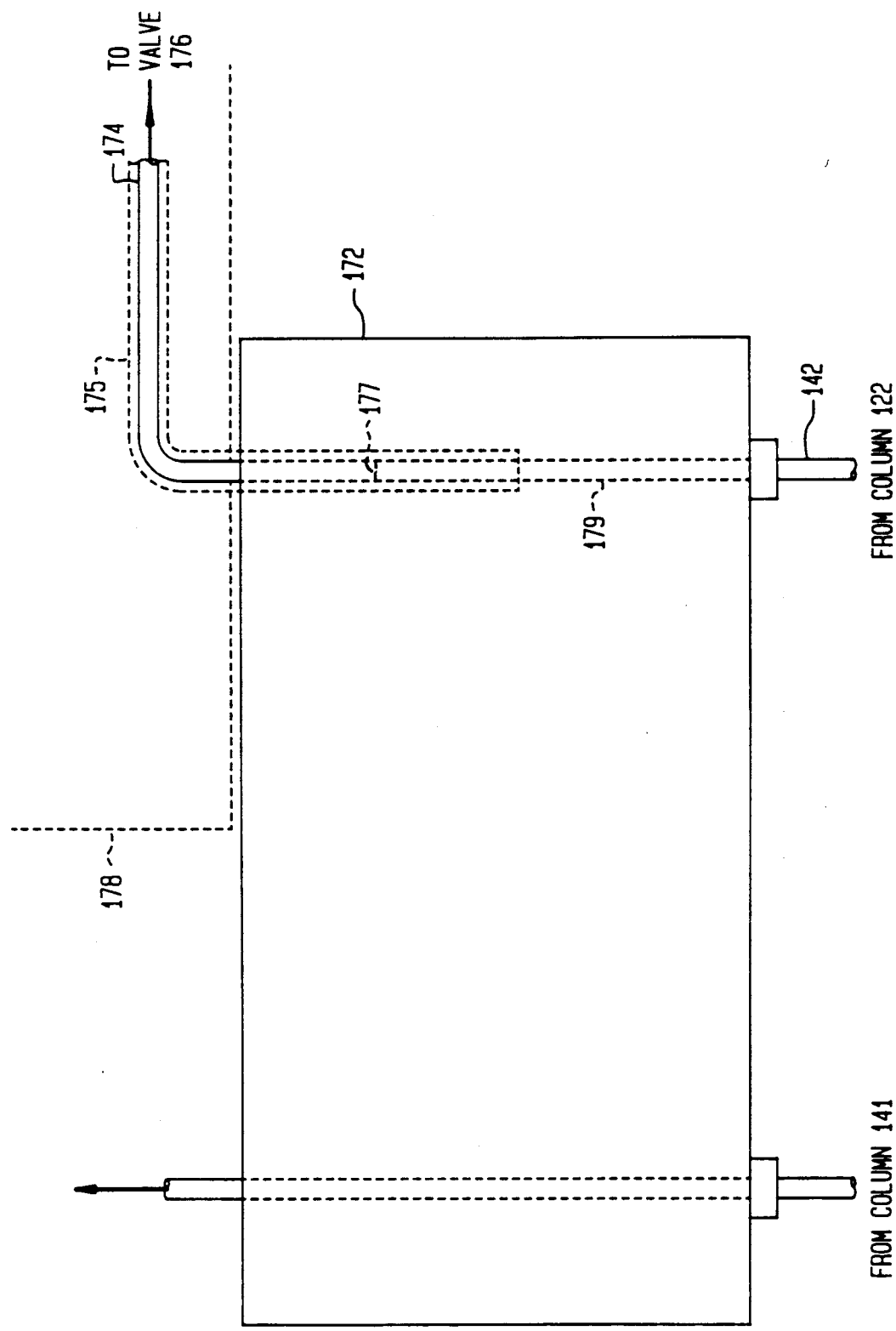

AUTOMATED PREPARATIVE GAS CHROMATOGRAPH

This is a division of application Ser. No. 07/160,541 filed Feb. 25, 1988.

BACKGROUND OF THE INVENTION

A. Field of the Invention

This invention relates to gas chromatograph systems.

B. Background Art

It is known in the art to flow a carrier gas from a source through tubing to carry a sample to be analyzed into a gas chromatographic system. The carrier gas carries the sample from an injector where it been volatilized into an analytical column. The column effluent then flows to a thermal conductivity detector for subsequent analysis. The effluent from the thermal conductivity detector may then be separated and the separated portions of the effluent may be directed to a waste trap or to one of a plurality of collection traps.

However, conventional preparative-scale gas chromatographic systems have had difficulties in functioning adequately with chemicals having very low volatilities such as alkyl toluenediamines. Such chemicals may be solid at room temperature and are particularly difficult to isolate from process reaction mixtures in sufficient quantities and purities for molecular characterization. These compounds have tended to solidify and block valves and conduits throughout the gas chromatographic system with a hard, viscous condensate. They have also exhibited very aggressive characteristics towards the materials and elements of the system.

Inadequate vaporization of these low volatility components in the injector has caused samples to remain in the injector port and subsequently clog the injector. In addition, low volatility has also resulted in insufficient sample material being introduced into the column It was also observed that carry-over was experienced from one injection to the next.

Additionally, very low collection efficiency of the isolated components was observed The design of the collection system encouraged aerosoling of separated components and subsequent loss to the environment. Low volatility components are particularly susceptible to this aerosoling phenomenon.

In addition to blockage of injector ports, blocking of the conduits and valves within the collection and separation system was a serious problem. Prior systems provided a conduit with a flow of carrier gas connected to this system to flush and clean the system. Thus, the carrier gas could be directed through the valves and conduits of the separation and collection system for cleaning. However, when low volatilitY. compounds such as alkyl toluenediamines solidify and deposit hard. viscous condensate within the conduits and the valves the carrier gas could not remove them. Thus the collection and separation systems had to be frequently dismantled to be cleaned in order to prevent the residue of previous analytes from interfering with later results.

Another area of difficulty for very low volatility compounds was observed at the outlet of the thermal conductivity detector of gas chromatographic A conduit was provided for the flow of effluent from the outlet of the thermal conductivity detector to the separation and collection system. However, the connection between the conduit and the thermal conductivity detector outlet was a source of heat loss leading to a "cold spot." Low volatility compounds had a tendency to condense at the "cold spot."

When these materials finally passed through the system to condensation tubes there was excessive aerosoling in the tubes as previously described. This lead to inefficient condensation and collection of sample components which was particularly undesirable in isolating components that are only available in extremely low concentrations. :t has been known in the art to block the end of the condensation tube with a quantity of glass wool to decrease aerosoling. While this helped with the aerosoling problem, a portion of the separated material which was being collected would condense on the glass wool. This further contributed to a decrease in collection efficiency since material condensed on the glass wool rather than on the condensing tube could not be easily recovered. In addition, the presence of the glass wool could lead to blockage of the condensation tube when sufficient material condensed on the glass wool.

SUMMARY OF THE INVENTION

A gas chromatographic system has conduits and valves adapted for analysis and collection of low volatility effluent. An injection site is provided for alternately supplying liquid solvent for removing condensed effluent from the system when the flow of effluent is terminated. Conduits are joined within the thermal conductivity detector of the system to prevent condensation at the joint. Conduits are provided with copper jackets which are coupled to sources of thermal energy to prevent condensation within the conduits. A trap filter provides backpressure in the collection system wherein recovery of condensed effluent in the filter is facilitated by the smooth surface of the filter.

BRIEF DESCRIPTION OF THE DRAWINGS

FIGS. 6A,B show a more detailed representation of the transfer lines of the system of FIG. 1;

FIG. 8 shows the connecting system of FIG. 7 provided with a junction internal to the detector

DETAILED DESCRIPTION OF THE INVENTION

Figure 1:
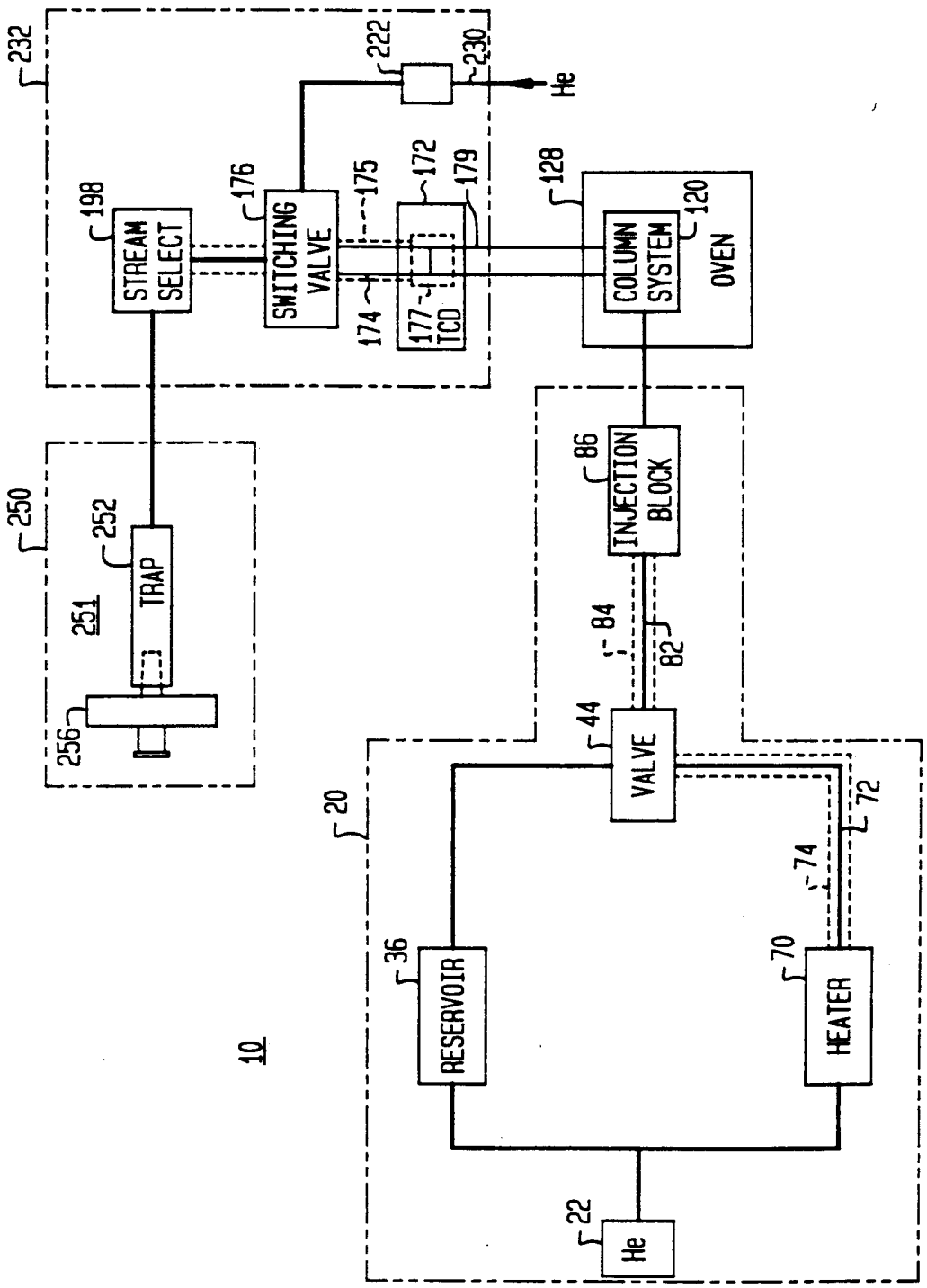
FIG. 1 is a simplified block diagram of the gas chromatographic system of the present invention.

Referring now to FIG. 1, there is shown a simplified block diagram of gas chromatographic system 10 of the present invention. Gas chromatographic system 10 includes sample injection system 20 for automatically injecting low volatility samples into gas chromatographic column system 120 as well as separation and collection system 232 and trap system 250.

Injection system 20 includes helium source 22 for providing a carrier gas for system 20. Helium gas from source 22 flows to reservoir 36 which contains a sample dissolved in a suitable organic solvent. The sample may be a low volatility compound such as an alkyl toluenediamine. The helium gas forces the sample from the reservoir to valve 44 for injection into column system 120 within column system oven 128

Helium gas from source 22 also flows to preheater 70 where it is heated and transmitted to valve 44 by way of nickel tubing or conduit 72. While passing through tubing 72, the thermal energy of the heated helium gas may be lost due to radiation from nickel tubing 72. Nickel tubing 72 is therefore encased or surrounded with copper jacket 74. Copper jacket 74 is thermally coupled with a source of thermal energy such as preheater 70. The thermal energy from the source of thermal energy is thus distributed over nickel tubing 72 by copper jacket 74 thereby preventing the contents of nickel tube 72 from cooling.

In a similar manner, thermal energy may be lost from the contents of nickel tubing 82 which transmits sample analyte from valve 44 to injection block 86. This may cause the temperature of the analyte within tubing 82 to drop somewhat. While this is acceptable for many high volatility analytes, this temperature gradient is undesirable for very low volatility analytes such as alkyl toluenediamines, as previously described. This temperature drop is unacceptable because it contributes to condensation of the analyte within nickel tubing 82 and blockage of nickel tubing 82.

Thus, nickel tubing 82 may be encased within copper jacket 84 and copper jacket 84 may also be thermally coupled to a source of thermal energy as previously described for nickel tubing 72 and copper jacket 74. For example, copper jacket 84 may be thermally coupled to injection block 86.

In a similar manner, low volatility analyte may condense in separation and collection system 232 after leaving column system 120. This may cause condensation of analyte, for example, in tube 174 which transmits analyte from thermal conductivity detector 172 to valve 176 within separation and collection system 232 as well as causing condensation within the ports of valve 176 and stream selection valve 198. Thus, the conduits of separation and collection system 232, such as nickel tubing 174, may also be encased within a copper jacket such as copper jacket 175. Copper jacket 175 may be coupled to a source of thermal energy. The temperature within tubing 174, as well as witin all other transfer lines of the system of the present invention may be in the range of approximately 200 to 300 degrees C.

It will be understood by those skilled in the art that any conduit within system 10 which may be blocked by condensation of low volatility specimen may in a like manner be surrounded by a copper jacket which is coupled to a source of thermal energy to prevent condensation within the conduit as well as to prevent condensation within the ports of the various valves of system 10. Furthermore it will be understood that only a portion of selected conduits may be encased by a copper jacket rather than the entire length of a conduit. The source of thermal energy to which a conduit or a portion of a conduit may be thermally coupled may be injection block 86 as previously described or column system oven 128 or any other source of elevated temperature.

In spite of heating the conduits of system 10, low volatility samples may still condense within, for example, separation and collection system 232. Therefore, separation and collection system 232 is provided with helium line 230 for transmitting helium gas to switching valve 176, stream selection value 198 and trap system 250 in order to clean condensate and contaminants from these elements. Thus condensate may be swept out of separation and collection system 232 by the helium. However, when extremely low volatility compounds such as alkyl toluenediamine condense in these elements of system 232. these compounds may form a hard, viscous material which is difficult to remove from the inner surfaces of conduits and valves using a helium gas sweep or flush.

Therefore, in order to avoid disassembling separation and collection system 232 for cleaning, system 232 is provided with injection site 222 in line 230 for providing a liquid solvent such as methanol to separation and collection system 232. The liquid solvent, provided by way of injection site 222, may thus pass through valve 176 stream selection value 198 and trap system 250 as well as all of the conduits therebetween to dissolve and clean out the condensed low volatility analytes. It will be understood by those skilled in the art that the choice of a liquid solvent depends on the sample condensed within separation and collection system 232 and that other liquid solvents besides methanol may therefore be injected into system 232 by way of injection site 222.

Effluent from column system 120 passes through thermal conductivity detector 172 to valve 176 after separation of sample constituents in column system 120. Tubing 179 of thermal conductivity detector 172 therefore transmits the effluent from thermal-conductivity detector 172 to the inlet of tubing 174 Thus, tubing 174 must be coupled to the outlet of conduit 179 of thermal conductivity detector 172 in order to receive the effluent for transmission to valve 176.

A coupling between tubing 174,179 may be a source of heat loss causing a "cold spot" at or near the point of coupling if the coupling is exterior to thermal conductivity detector 172. Low volatility analytes being transmitted past this "cold spot" may condense and block up tubing or conduits 174,179. Therefore, conduits 174,179 are joined within thermal conductivity detector 172 to prevent a source of heat leak. Conduits 174,179 may be joined by silver solder junction 177 within thermal conductivity detector 172 to evenly distribute heat and prevent condensation at the point of coupling.

After effluent has been separated by separation and collection system 232, it is transmitted to trap system 250. While trap system 250 is shown containing a single trap 251, it will be understood by those skilled in the art that a plurality of traps 251 may be included within trap system 250.

Effluent transmitted into condensing tube 252 of trap 251 may aerosol within condensing tube 252 thereby decreasing the efficiency of collection within trap system 250. Extremely low volatility compounds such as alkyl toluenediamines are especially subject to this aerosoling phenomenon Therefore. condensing tube 252 is provided with trap filter 256. Trap filter 256 provides a slight backpressure to decrease the aerosoling as well as a smooth non-porous surface to facilitate removal of condensate from trap filter 256 with a suitable solvent. Such a smooth non-porous surface may be provided by forming trap filter 256 from a material such as nylon.

Figure 2:
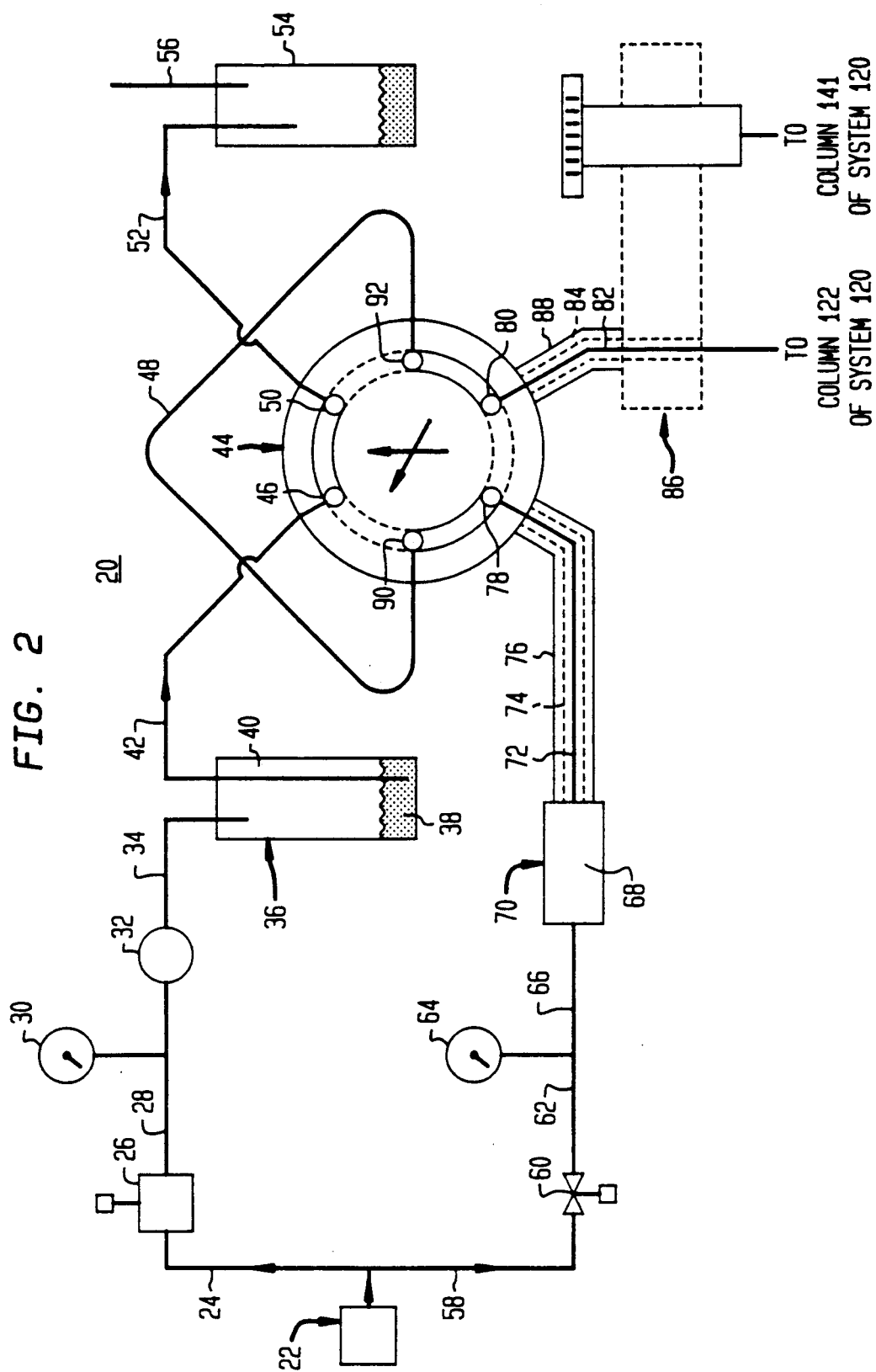
FIG. 2 shows in more detail a sample injection system used in the gas chromatographic system of FIG. 1.

Referring now to FIG. 2, there is shown in more detail injection system 20 for automatically injecting low volatility samples into gas chromatographic column 122 of column system 120 using pressurized helium as a carrier.

In system 20, helium from source 22 flows through copper tubing 24 to pressure regulator 26. Helium then flows through copper tubing 28 where its pressure is monitored by pressure gauge 30 Solenoid 32, depending on whether it is actuated, either stops the flow of helium or allows the flow of helium through stainless steel tube 34. If solenoid 32 is actuated, helium enters closed sample reservoir 36. where it forces sample 38 into stainless steel tube 40. Sample 38 in reservoir 36 is dissolved in a suitable organic solvent. Sample 38 then passes into tube 42 which is constructed of polytetrafluoroethylene.

Sample 38 dissolved in organic solvent then enters six-port valve 44 through port 46. Six-port valve 44 is adjusted to allow sample 38 to enter steel sample loop 48. The volume of stainless steel sample loop 48 is adjustable from twenty-five to one-thousand microliters with an optimum range of twenty-five to fifty microliters. It will be understood by those skilled in the art that selection of the correct volume of sample loop 48 can vary according to the concentration of sample 38. In addition, it will be understood by those skilled in the art that the concentration of sample in the appropriate solvent may be altered dependent on the concentration of the required analyte within the sample.

When sample loop 48 is filled excess sample 38 flows out of six-port valve 44 through port 50 and tube 52 and into sample recycle reservoir 54. Excess sample 38, still dissolved in organic solvent, which is collected in sample recycle reservoir 54 may be recovered for future use. Any helium carrier which entered sample recycle reservoir 54 escapes through stainless steel tube 56. When sample loop 48 is completely filled solenoid 32 is closed preventing more sample 38 from flowing into six-port valve 44.

Helium from source 22 also flows through copper tube 58 and through mass flow controller 60. Helium then flows through stainless steel tube 62 to pressure gauge 64 and through fitting 66 into coiled nickel tubing 68 within preheater 70. Helium is then heated to the desired temperature. It will be understood by one skilled in the art that the desired temperature depends on the sample 38.

Helium from preheater 70 enters nickel tubing 72 surrounded by copper jacket 74 and by woven fiberglass sleeve 76. Copper jacket 74 and woven fiberglass sleeve 76 help prevent heat loss to the environment. The heated helium from nickel tubing 72 then enters six-port valve 44 through port 78. Heated helium exits six port valve 44 through port 80 and enters nickel tubing 82. The heated helium then enters chromatographic column 122 of column system 120.

Nickel tubing 72 is encased within copper tube or a jacket 74 and woven fiberglass sleeve 76. Copper jacket 74 is in physical contact with the preheater 70. Thus, copper jacket 74, thermally coupled to preheater 70, receives thermal energy from preheater 70 and distributes the thermal energy along the length of nickel tubing 72 causing nickel tubing 72 to be maintained substantially at the temperature of preheater 70. When nickel tubing 72 is maintaiend at this elevated temperature, the helium gas flowing through nickel tubing 72 is also maintained at an elevated temperature.

Six-port valve 44 then rotates to its sample inject position In the sample inject position of valve 44, heated helium entering six port valve 44 at port 78 enters sample loop 48 through port 90, preheating sample 38 and driving it back into six-port valve 44 through port 92. When sample 38 exits six port valve 44 through port 80, it enters nickel tubing 82. Sample 38 then enters chromatographic column 122 where it is separated into its component parts.

Without suitable insulation, significant heat loss from nickel tubing 82 is inevitable. This may cause the temperature of the specimen within the tubing 82 to drop significantly. While this temperature drop is acceptable for many high volatility specimens for very low volatility compounds such as alkyl toluenediamines. It was observed to contribute to condensation of specimen within nickel tubing 82. This condensation causes blockage of tubing 82 and also of port 80 of valve 44.

Thus nickel tubing 82 is encased within copper tube or jacket 84 and woven fiberglass sleeve 88. Copper jacket 84 is in physical contact with heated injector block 86. Thus, copper jacket 84, thermally coupled to block 86, receives thermal energy from block 86 and distributes the thermal energy along the length of nickel tubing 82 causing nickel tubing 82 to be maintained substantially at the temperature of block 86 When nickel tubing 82 is maintained at this elevated temperature, sample 38 is prevented from condensing and blocking nickel tubing 82 and from blocking port 80 of six-port valve 44.

Figure 3:
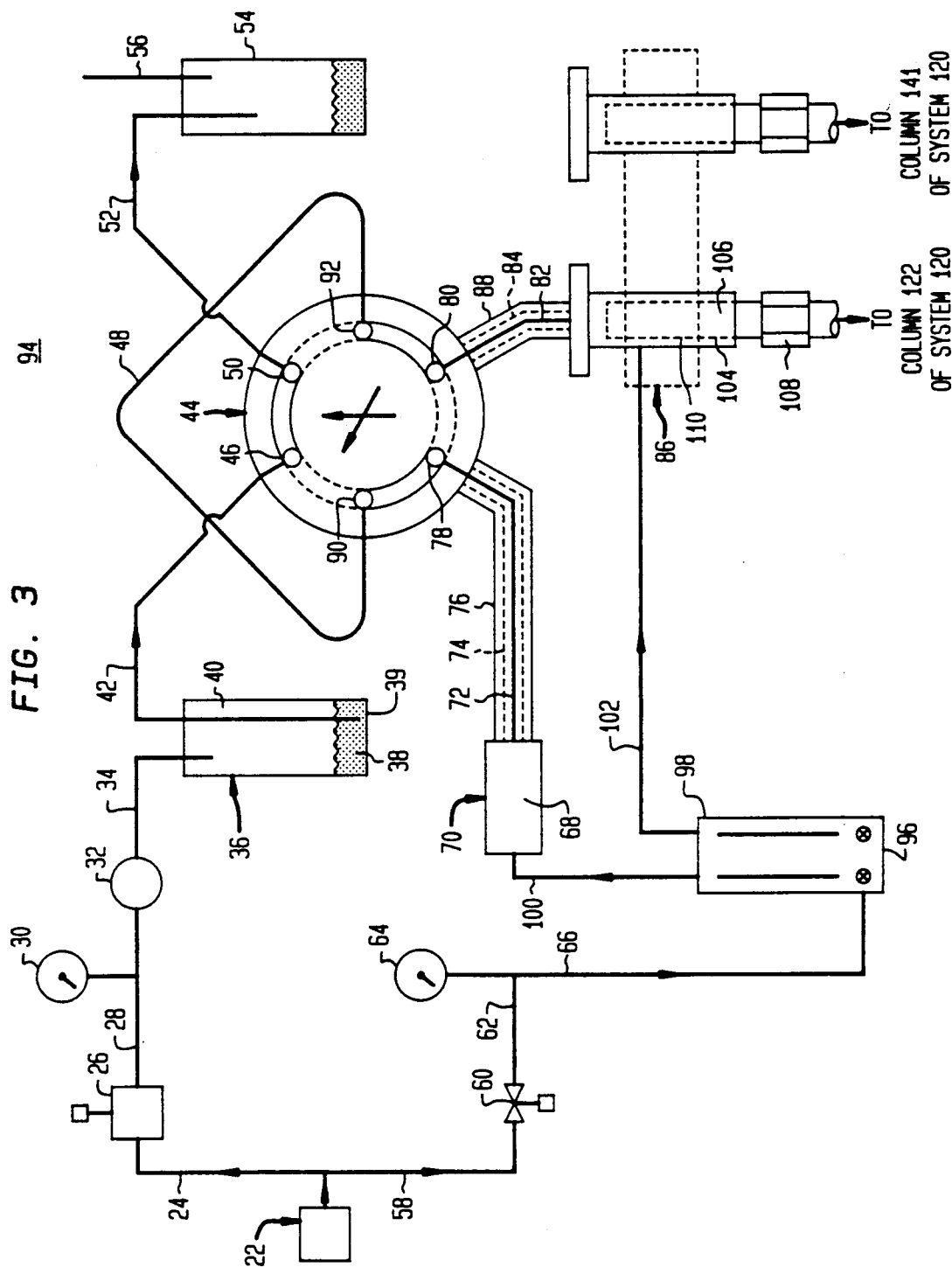
FIG. 3 shows an alternate embodiment of the sample injection system of FIG. 2.

Referring now to FIG. 3. there is shown injection system 94 of the present invention for automatically injecting very low volatility samples into a gas chromatographic column at a uniform predetermined temperature using pressurized helium as a carrier. Injection system 94 is an alternate embodiment of injection system 20.

Helium from source 22 flows through copper tubing 24 to pressure regulator 26 and through copper tubing 28 to pressure gauge 30 as previously described for system 20. Solenoid 32, depending on its position, either stops the flow of helium or allows the flow of helium through stainless steel tube 34. If solenoid 32 is in an open position, helium then enters sample reservoir 36, where it forces the sample 38 into stainless steel tube 40 all as described for system 20. Sample 38 in sealed reservoir 36 is dissolved in a suitable organic solvent. Sample 38. diluted to a range of approximately 5 to 50 weight percent then passes into polytetrafluoroethylene tube 42.

Sample 38 dissolved in organic solvent then enters six-port valve 44 through port 46. Six-port valve 44 is adjusted to allow sample 38 to enter stainless steel sample loop 48. The volume of stainless steel sample loop 48 may be adjusted from twenty-five to one thousand microliters. It will be understood by those skilled in the art that the correct volume may vary according to the concentration of sample 38. In addition it will be understood by those skilled in the art that the concentration of sample in the appropriate solvent may be altered.

dependent on the concentration of the required analyte within the sample.

When sample loop 48 is filled excess sample 38 flows out of six-port valve 44 through port 50 through tube 52 and into sample recycle reservoir 54. Excess sample 38 still dissolved in organic solvent collected in sample recycle reservoir 54 may be recovered for future use by recycling to primary reservoir 36. Any helium which enters sample recycle reservoir 54 escapes through stainless steel tube 56. When sample loop 48 is completely filled solenoid 32 is closed, preventing more sample 38 from flowing into six-port valve 44, all as previously described for system 20.

Helium from source 22 also flows through copper tube 58, through mass flow controller 60 and through stainless steel tube 62, to pressure gauge 64. From stainless steel tube 62 helium flows through fitting 66 into union tee 96 and into dual rotameter 98. Here the flow of helium from source 22 by way of tube 62 is divided into two streams.

Proceeding now through stainless steel tubing 100 into coiled nickel tubing 68 within preheater 70, helium is heated to the desired temperature. It will be understood by those skilled in the art that the desired temperature depends on the sample.

Helium from preheater 70 enters nickel tubing 72. Nickel tubing 72 is encased within copper tubing or jacket 74. Copper jacket 74 is in physical contact with preheater 70. Thus copper jacket 74, thermally coupled to preheater 70, receives thermal energy from preheater 70 and distributes this thermal energy along the length of nickel tubing 72 causing nickel tubing 72 to be maintained at the temperature of preheater 70. When nickel tubing 72 is maintained at an elevated temperature, the helium carrier gas flowing through nickel tubing 72 is also maintained at an elevated temperature. The heated helium from nickel tubing 72 enters six-port valve 44 through port 78.

Proceeding now from dual rotameter 98 to nickel tubing 102, helium is carried by nickel tubing 102 into injector body 110, where it comes in contact with glass insert 104. Glass insert 104 is directly connected by union 108 with chromatographic column 122. This second stream of helium carrier gas to the injector sweeps the injector body to flush residual volatilized sample from the injector onto the chromatographic column.

Six-port valve 44 is then rotated to its sample inject position, as shown In the inject position of valve 44, heated helium entering six-port valve 44 now enters sample loop 48 through port 90, preheating sample 38 and driving it back into six-port valve through port 92. Sample 38 then exits six-port valve 44 through port 80. Sample 38 enters nickel tubing 82 and is carried into the injector body 110 where it comes in contact with glass insert 104. Which is loosely packed with glass wool 106. Sample 38, still dissolved in organic solvent, is then fully vaporized, and enters chromatographic column 122, where it may be analyzed. Condensation of sample 38 in nickel tubing 82 and blockage of nickel tubing 82 and port 80 of six-port valve 44 is prevented due to maintenance of the temperature of sample 38 while sample 38 is passing through tubing 82.

Figure 4:
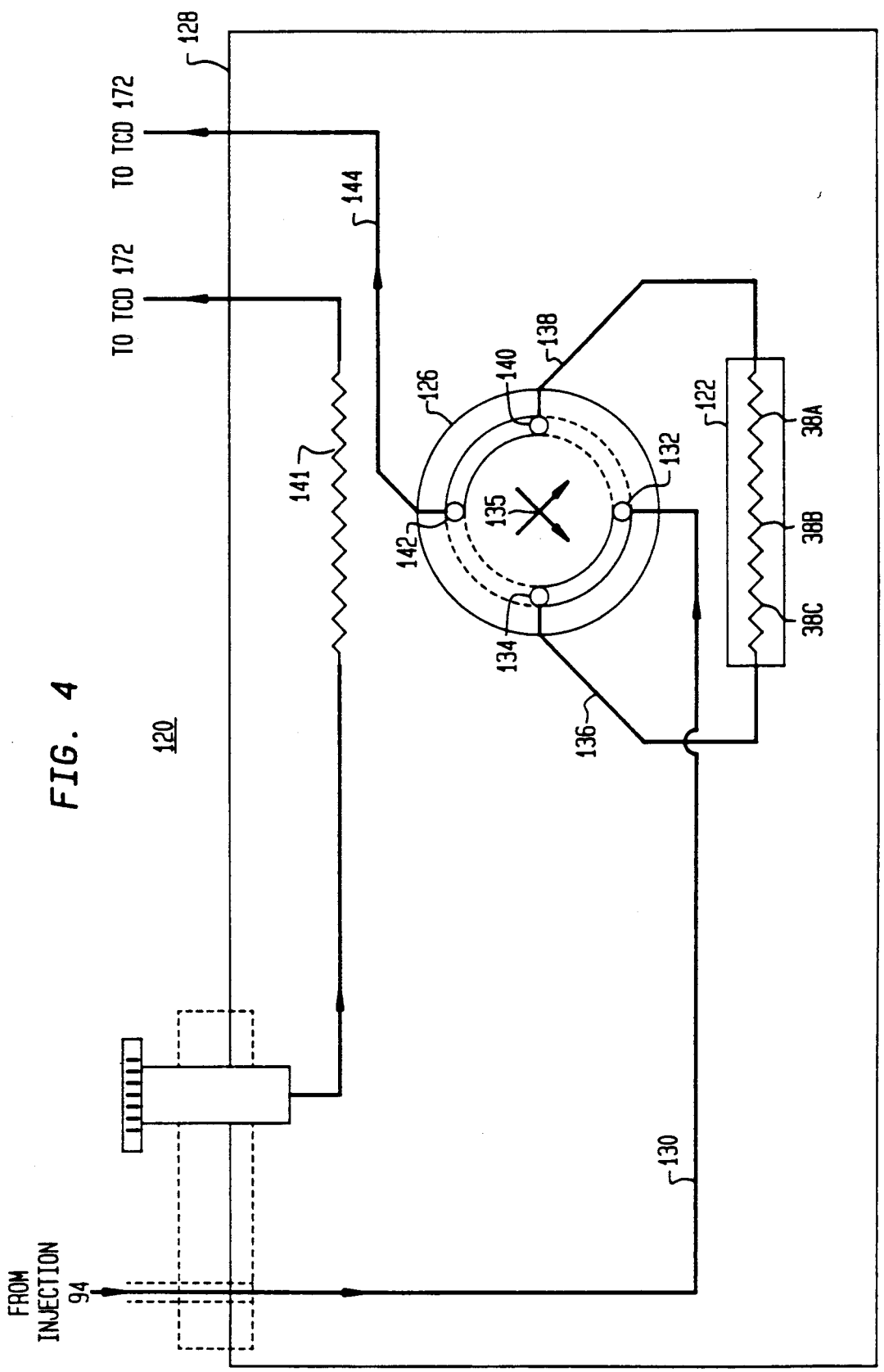
FIG. 4 shows a more detailed representation of the column backflush of the gas chromatographic system of FIG. 1.

Referring now to FIG. 4, there is shown heated chromatographic column backflush device 120. Heated column backflush device 120 allows components of higher molecular weight to be backflushed from the chromatographic column 122 without traveling through the entire length of chromatographic column 122.

Sample 38 enters chromatographic oven 128 by way of nickel tubing 130. Sample 38 then enters four-port valve 126, also located within chromatographic oven 128. Sample 38 enters four-port valve 126 through port 132. When four-port valve 126 is in sample inject position shown, sample 38 exits fourport valve 126 through port 134. Sample 38 then flows through nickel tubing 136 into gas chromatographic column 122, where sample 38 is separated into components 38A,B,C. As understood by those skilled in the art, component 38A is of relatively lower molecular weight, component 38B is of medium molecular weight, and component 38C is of relatively higher molecular weight.

While four port valve 126 is in sample inject position, the separated components 38A,B,C of sample 38 flow into nickel tubing 138 in the following order: first component 38A. followed by component 38B and finally component 38C. These components enter four port valve 126 through port 140. They then exit four-port valve 126 through port 142 and flow through nickel tubing 144.

After sample 38 has entered chromatographic column 122, four-port valve 126 may be rotated to position as indicated by arrow 135. When four-port valve 126 is in backflush position helium carrier gas entering four-port valve 126 at port 132 exits at port 140. Helium carrier gas then enters nickel tubing 138. The flow of this carrier gas entering nickel tubing 138 and chromatographic column 122 elutes component 38C from chromatographic column 122 and into nickel tubing 136. Component 38C then enters four-port valve 126 through port 134 and exits through port 142. Component 38C then exits backflush system 120 by way of nickel tubing 144. Thus high molecular weight component 38C which may not be of analytical interest, can be more quickly eluted from chromatographic column 122.

Figure 5:
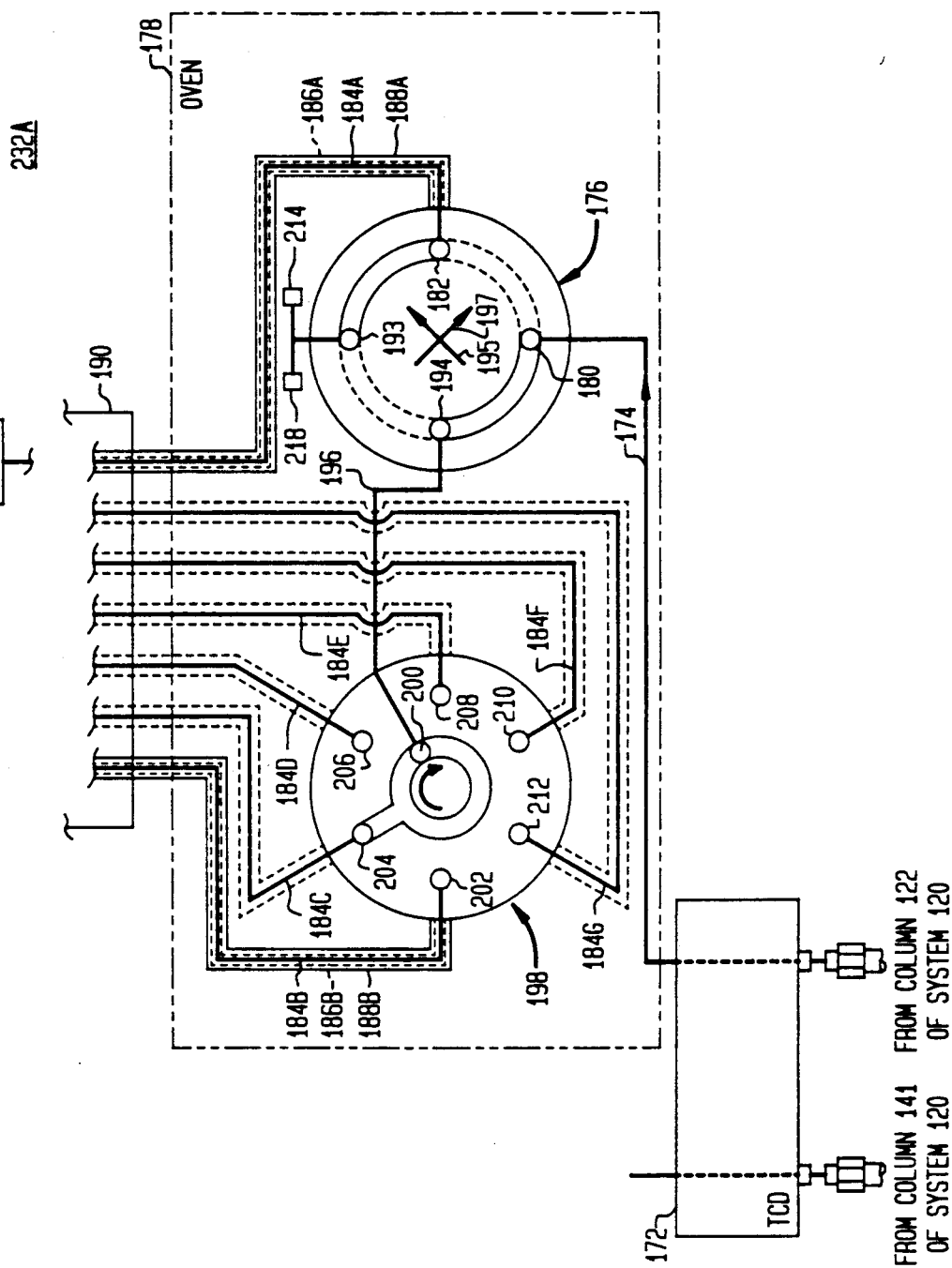
FIG. 5 shows a more detailed representation of the separation and collection system of the gas chromatographic system of FIG. 1 without a bulkhead union for injection of solvent.

Referring now to FIG. 5, there is shown collection and separation system 232A for separation of chromatographic column effluent. System 232A allows chromatographic column effluent to be separated into individual components and collected. System 232A does not include bulkhead union 222 of FIG. 6 which will later be described.

Effluent flows from thermal conductivity detector 172 into nickel tubing 174, and into four-port valve 176 by way of port 180. Valve 176 is located within heated valve oven 178 shown by the dotted lines. While valve 176 is in its bypass position indicated by arrow 195, effluent flows out of valve 176 through port 182 and into stainless steel tubing 184A located within cooper tubing 186A and fiberglass sleeve 188A.

Copper tubing 186A maintains stainless steel tubing 184A at an elevated temperature as previously described, and fiberglass sleeve 188A insulates copper tubing 186A against heat loss to the environment. All copper jackets within heated valve enclosure 178 are thermally coupled to an aluminum block (not shown) which serves as a mounting and a heater for valves 176.198. Waste effluent then passes through stainless steel tubing 184A which is partially encased within heated aluminum block 190. Heated aluminum block 190 prevents condensation of effluent. Effluent then passes into waste trap 192, where it is condensed.

When thermal conductivity detector 172 detects elution from chromatographic column 122 of a component of analytical interest the four-port valve 176 is rotated to select position, indicated by arrow 197. Valve 176 is activated automatically by the gas chromatograph through external electrical relays (not shown) as understood by those skilled in the art.

After valve 176 is switched to the select position effluent flows out of port 194 and into nickel tubing 196. Effluent then flows into seven-position, stream selection valve 198 through port 200. Seven-port stream selection valve 198 is also located within heated valve oven 178. Selection valve 198 is rotated to distribute various components of the effluent stream which have been separated in chromatographic column 122. Valve 198 is rotated so that components exit through a selected one of ports 202. 204. 206. 208 210. 212 Seven-port valve 198 is activated automatically by the gas chromatograph of the present invention by means of external electrical relays (not shown). as understood by those skilled in the art Depending on which port of seven port valve 198 is selected, an effluent component flows through stainless steel tubing 184B, 184C, 184D, 184E, 184F 184G, enclosed in copper tubing 186B, 186C, 186D, 186E, 186F, 186G respectively and fiberglass sleeve 188B, 188C, 188D, 188E, 188F, 188G respectively.

The effluent within stainless steel tubing 184B-G enters heated aluminum block 190 which prevents effluent condensation. The separated components of the effluent from chromatographic column 122 may then be collected.

When four-port valve 176 is rotated so that effluent flows to seven-port valve 198, helium from helium source 214 enters valve 176 through port 193 and flows out of port 182 through stainless steel tubing 184A and into waste trap 192. This flow prevents backstreaming of wastes collected in waste trap 192 and subsequent contamination of valve 176. Helium source 214 may be replaced by solvent source 218. When solvent source 218 is connected to port 193, valve 176 may be rotated to select allowing solvent to flow to seven-port valve 198. Rotating valve 198 through its selection cycle then causes solvent to flush valve 198 and attached stainless steel tubing 184B-G. This allows cleaning of device 198 without disassembly.

Figure 6:
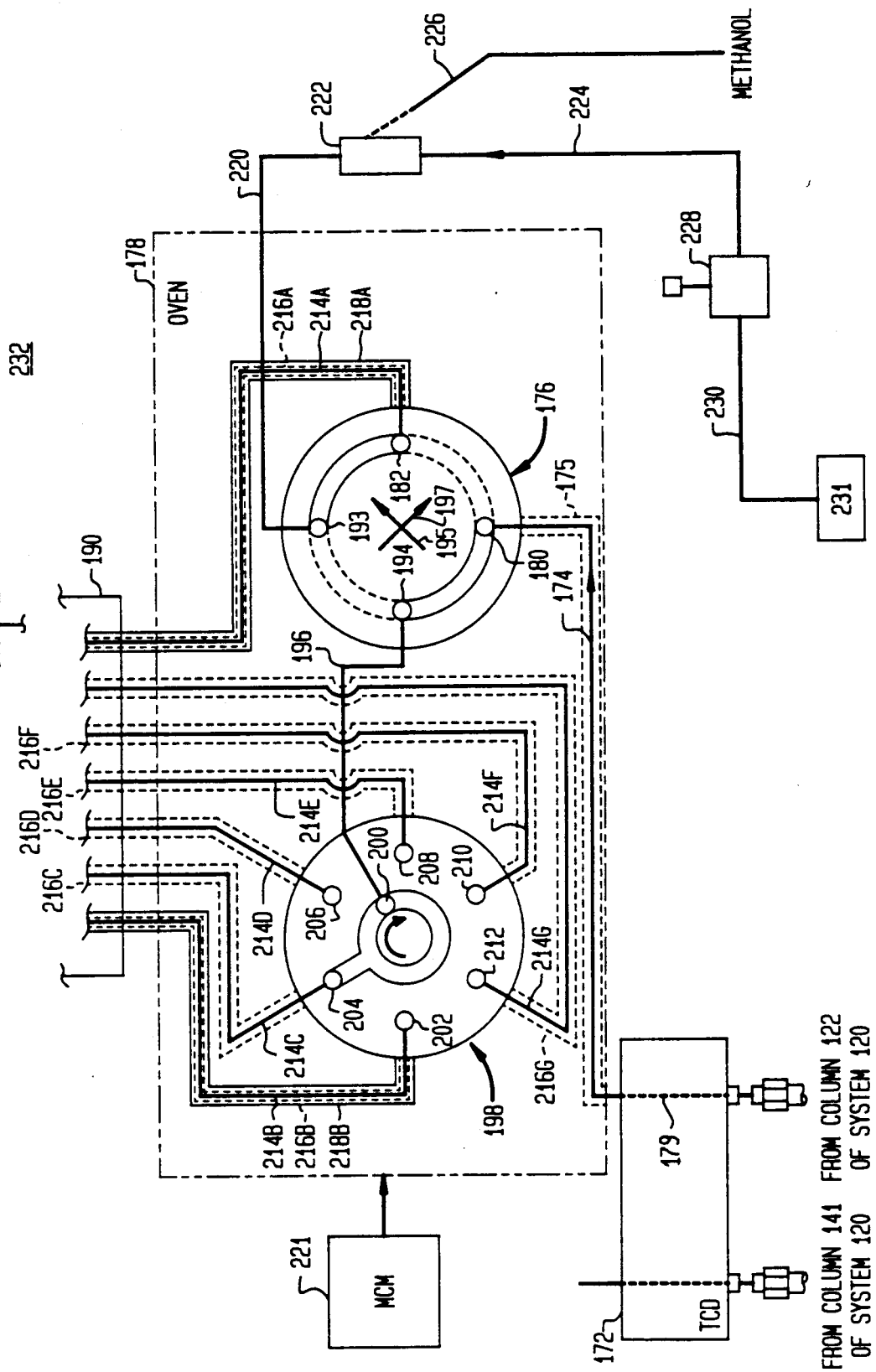
FIG. 6 shows the separation and collection system of FIG. 5 and the bulkhead union for injection of solvent as also shown in FIG. 1.

Referring now to FIG. 6, there is shown separation and collection system 232, separation of chromatographic column effluent including separation and collection system 232 along with injection site 222. System 232 allows chromatographic column effluent to be separated into individual components and collected.

Effluent flows from thermal conductivity detector 172 into nickel tubing 174 which is located within copper tubing 175. Copper tubing 175 is directly connected to aluminum heating block of valve oven 178. This allows heat from valve oven 178 to conduct along copper tubing 175 and prevents specimens within nickel tubing 174 from condensing. Nickel tubing 174 is directly silver soldered to exit line 179 of thermal conductivity detector 172. Nickel tubing is connected to four-port valve 176 by way of 180. Valve 176 is located within heated valve oven 178. While valve 176 is in bypass position, indicated by arrow 195, effluent flows out of valve 176 through port 182, into nickel tubing 214A located within copper tubing 216A and fiberglass sleeve 218A. Copper tubing 216A which is in thermal contact with heated valve oven 178, maintains nickel tubing 214A at elevated temperature, and fiberglass sleeve 218A insulates copper tubing 216A against heat loss to the environment. Effluent then passes through nickel tubing 214A which is encased by heated aluminum block 190. Heated aluminum block 190 prevents condensation of effluent in tubing 214A. Effluent then passes into waste trap 192 where it is condensed.

When thermal conductivity detector 172 detects elution from chromatographic column 122 of a component of analytical interest, four-port valve 176 is rotated to select position indicated by arrow 197. Valve 176 is activated automatically by gas chromatograph through external electrical relays as understood by those skilled in the art.

After valve 176 is switched to select position, effluent flows out of port 194 and into nickel tubing 196 Effluent then flows into seven-port stream selection valve 198 through port 200. Seven-port stream selection valve 198 is also located within hated valve oven 178. Valve 198 is rotated to distribute various components of effluent stream which have been separated in chromatographic column 122. Valve 198 may be rotated so that components exit through ports 202. 204, 206. 208. 210, 212. Sevenport valve 198 is activated automatically by the gas chromatograph through external electrical relays as understood by those skilled in the art. Depending on port of seven-port valve 198 selected, effluent component flows through nickel tubing 214B, 214C, 214D, 214E, 214F, 214G, enclosed in copper tubing 216B, 216C, 216D, 216E, 216F, 216G and fiberglass sleeve 218B, 218C, 218D, 218E, 218F 218G.

Effluent, within nickel tubing 214B-G, enters heated aluminum block 190. Heated aluminum 190 block prevents effluent condensation. The separated components of effluent from chromatographic column 122 may then be collected by a plurality of condensation traps.

When four-port valve 176 is rotated so that effluent flows to seven port valve 198, helium from helium source 231 is allowed to flow through copper tubing 230 into pressure regulator 228, set to pressure understood by those skilled in the art. Helium then flows through copper tubing 224 into bulkhead union 222 and then through stainless steel tubing 220 into valve 176 through port 193. Helium then flows out of port 182, through nickel tubing 214A and into waste trap 192. This flow prevents backstreaming of wastes collected in waste trap 192 and subsequent contamination of valve 176. During the helium sweep of system 232, valves 176, 198 are controlled by conventional multiposition control module 221 in a conventional manner.

When system 232 is used to separate and collect low volatility compounds, the helium sweep may not be adequate to remove all of the contaminants in the system during the cleanup process between analyses. This is so because these contaminants may be hard, viscous substances which adhere to the inner surfaces of system 232. Therefore, tubing 224 is provided with bulkhead union 222 for detaching tubing 224 from system 232 and terminating the flow of helium. Tubing 226 may then be attached to union 222. Tubing 226 provides a flow of a liquid solvent for dissolving and flushing away low volatility condensate within system 232. The liquid solvent may be any solvent appropriate for dissolving these compounds, for example methanol.

When tubing 226 is joined to bulkhead union 222 and a flow of methanol is provided by way of tubing 220 valves 176.198 may be rotated through their various positions under the control of multiposition control module 221 to supply a flow of solvent to all conduits and ports which could receive the helium sweep in a conventional manner. For example, when tubing 226 is connected to union 222, valve 176 may be rotated to its bypass condition, allowing solvent to flow to sevenport valve 198 Rotating stream select valve 198 through its selection cycle causes solvent to flush valve 198 and attached tubing 214B-G This allows cleaning of separation and collection system 232 without disassembly.

Additionally many low volatility compounds such as alkyl toluenediamines are observed to be very aggressive toward some materials of valve construction Thus, for example, valve 198 is formed of Hastalloy C which can resist these compounds.

Examples of the compounds for which the system of the present invention are suitable include alkyl toluenediamines, ethoxy alkyl toluenediamines. alkyl phenylenediamines alkyl toluidines, alkyl and cycloalkyl anilines and alkyl and cycloalkyl methylene dianilines. Generally, it is suitable for substituted aromatic amines which are highly polar and have low volatilities The composition of Nitronic 60, the material used in construction of four-port switching valve 176, is carbon. 0.1 percent maximum; silicon, 3.5–4.5 percent; nickel, 8–9 percent; iron, bulk; manganese, 7–9 percent; chromium, 16–18 percent; nitrogen, 0.08–0.18 The materials used in construction of the body of the valves could be any composition provided that the material is compatible with the high temperatures used in the instrument, and also that the material is inert to the chemical compounds involved. The composition of the valve rotor is of prime importance, since the rotor is in direct contact with the analytes.

Referring now to FIGS. 6A–B, there is shown a more detailed representation of tubing 174. Tubing 174 may be an approximately one-sixteenth inch outer diameter nickel tube with an inner diameter of approximately 0.01 to 0.02 inches. Copper jacket 175 surrounding tubing 174 may have an outer diameter of one-eighth inch and an inner diameter of approximately 0.07 inch Woven fiberglass sleeve 175A surrounds copper jacket 175. It will be understood by those skilled in the art that these dimensions may vary, and that the structure shown is applicable to other tubes and copper jackets within the system of the present invention.

Figure 7:
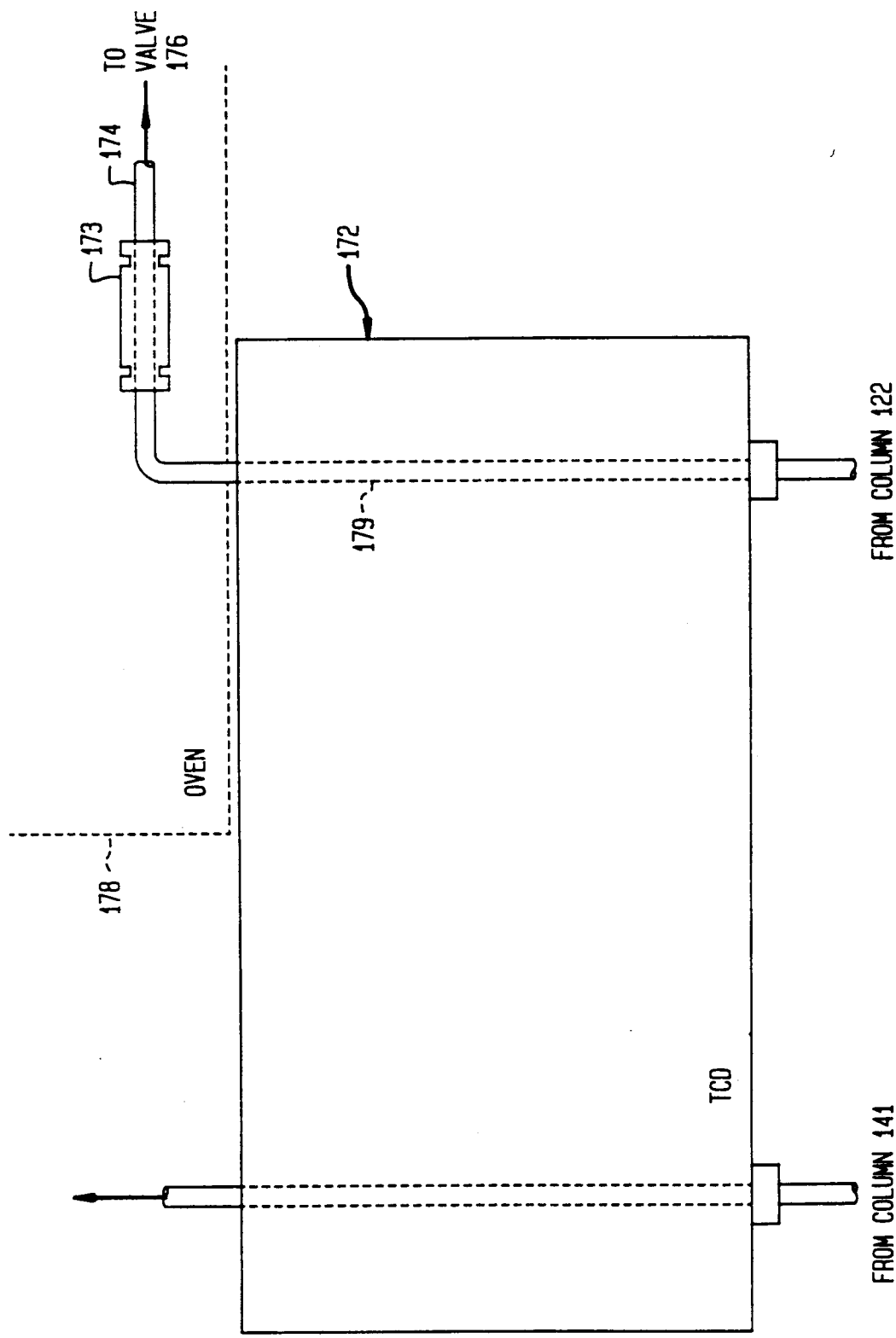
FIG. 7 shows a conventional system for connecting the thermal conductivity detector to the sample and collection system of the gas chromatographic system of FIG. 1 without a junction internal to the detector.

Referring now to FIG. 7, there is shown a system for connecting tube 179 carrying effluent through thermal conductivity cell 172 with tubing 174 which then carries the effluent to valve 176. Fitting 173 external to thermal conductivity detector 172 may be used to couple tubing 179 to tubing 174. However, fitting 173 may radiate heat and cause a "cold spot" at the junction of tubing 174.179. When effluent containing low volatility specimen passes this "cold spot," the specimen may condense and block the tubing.

Referring now to FIG. 8, there is shown an alternate embodiment of the attachment of FIG. 7. In this embodiment, tubing 174 is extended to the interior of thermal conductivity detector 172 and joined to tubing 179 within thermal conductivity detector 172. This system avoids the use of fitting 173 by joining tubing 174 to tubing 179 within thermal conductivity detector 172. Avoidance of fitting 173 exterior to detector 172 is desired for low volatility compounds because fitting 173 may be a source of heat loss causing a "cold spot" and low volatility compounds may condense at this "cold spot" and block conduits 174,179. The joining of conduits 174.179 may be accomplished by silver solder 177. Tubing 174 may then be enclosed in copper jacket 175 as previously described to completely eliminate the cold spot.

Figure 8A:
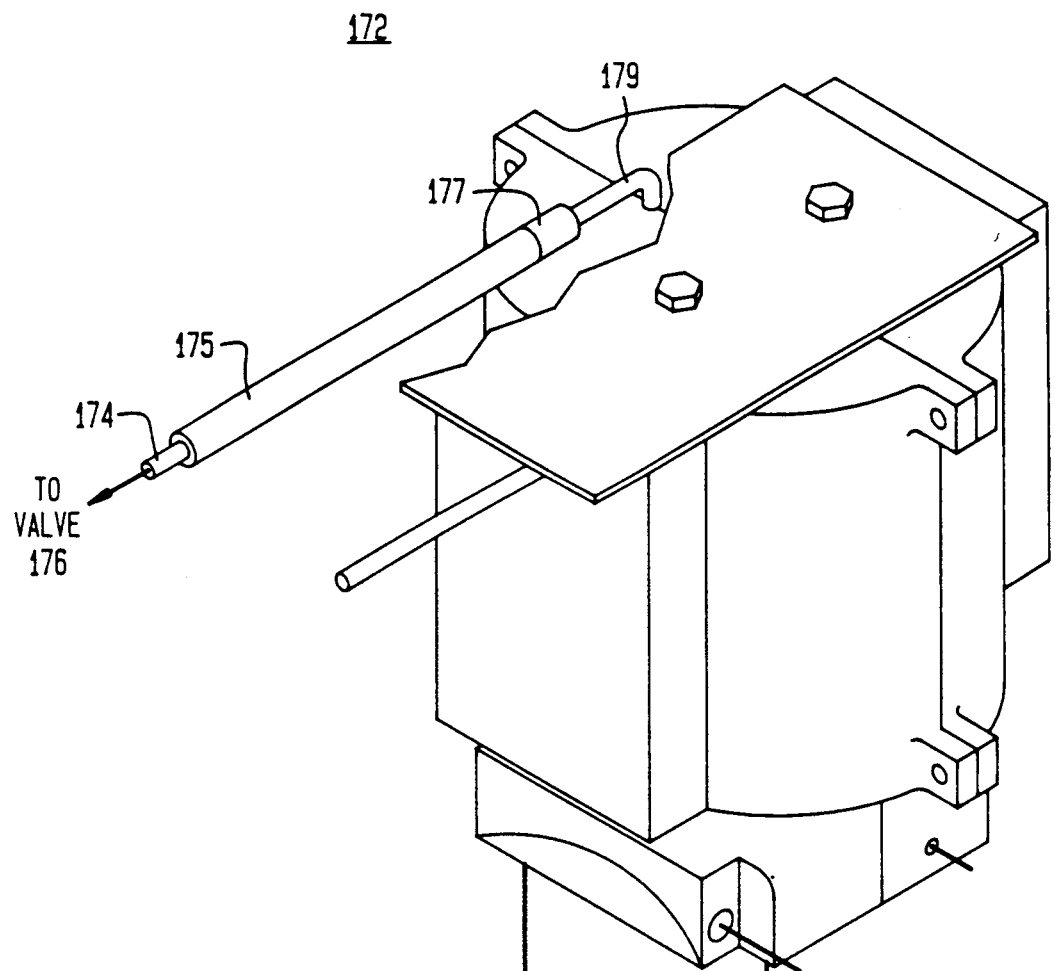
FIG. 8A shows the thermal conductivity detector of the gas chromatographic system of FIG. 1.

Referring now to FIG. 8A. there is shown a more detailed representation of thermal conductivity detector 172 in partial cutaway. Silver solder joint 177 is within thermal conductivity detector 172 to prevent a cold spot where tubing 174 joins tubing 179. It will be understood by those skilled in the art that the system of the present invention may include any non-destructive detector in place of thermal conductivity detector 172 for monitoring column effluent.

Figure 9:
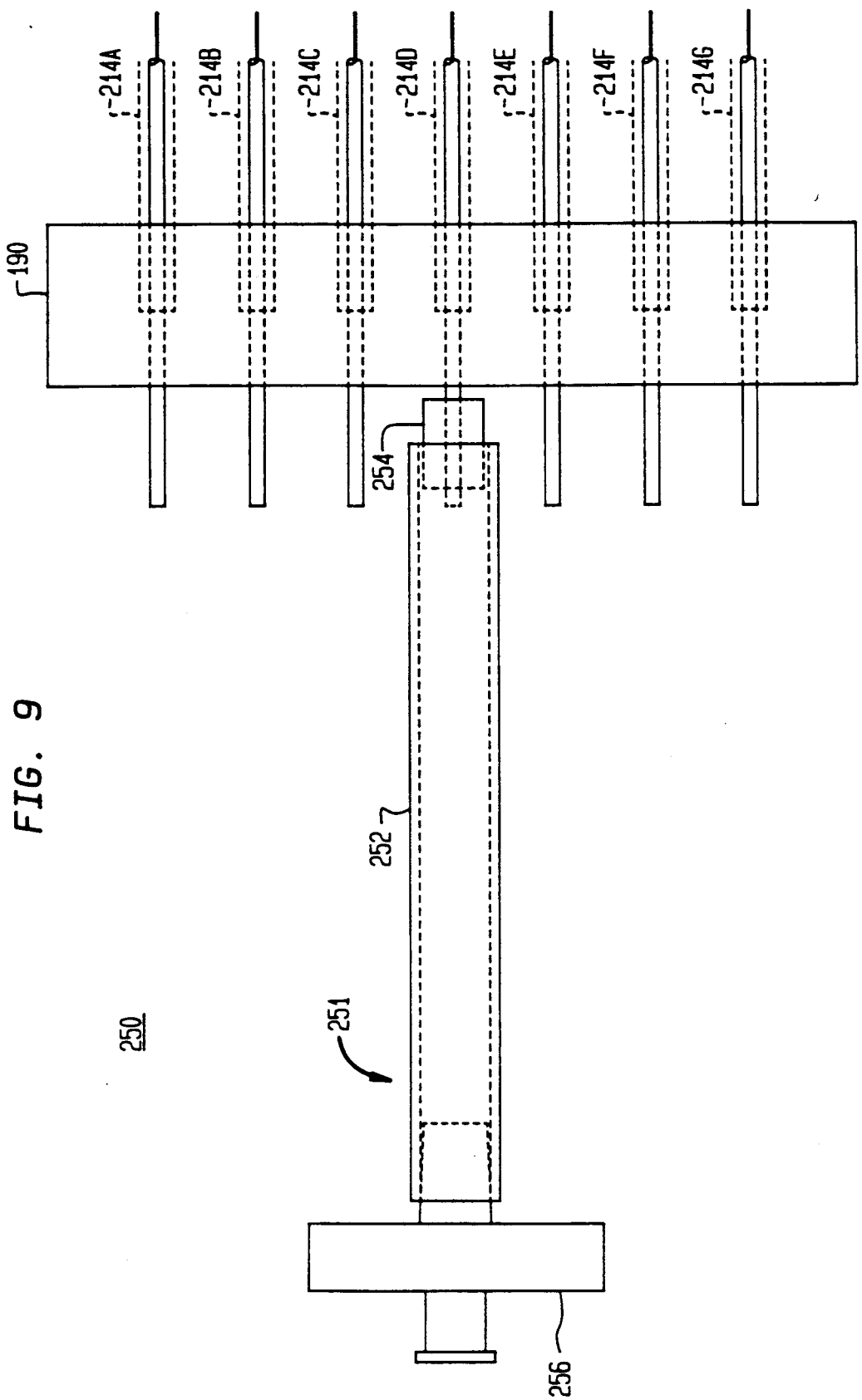
FIG. 9 shows a collection trap system of the gas chromatographic system of FIG. 1.
Figure 10B:
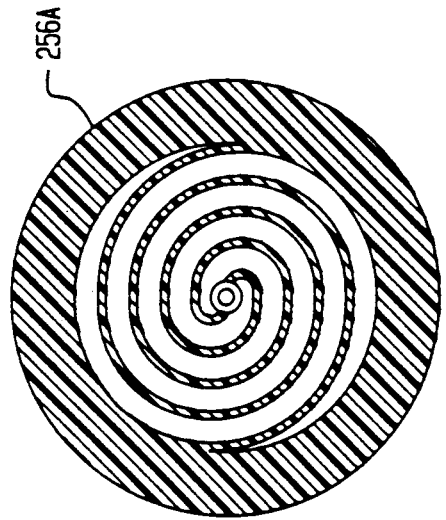
Figure 10C:
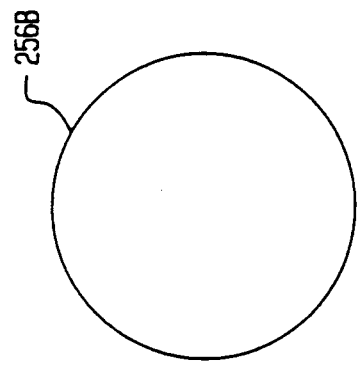
Figure 10D:
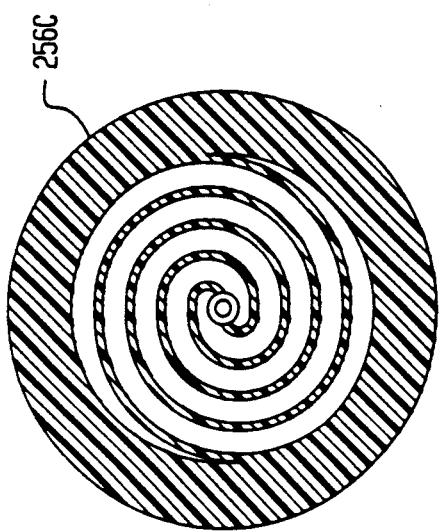
Figure 10E:
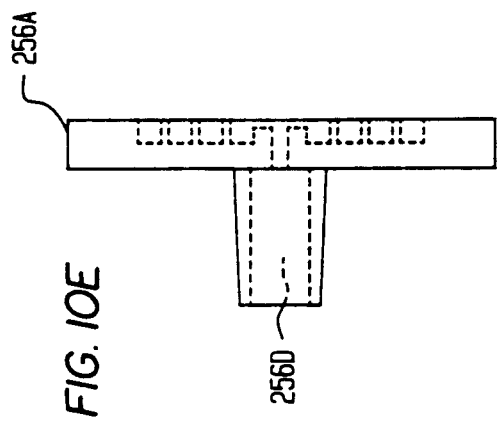
Figure 10F:
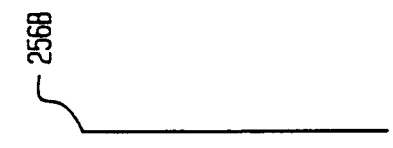
Figure 10G:
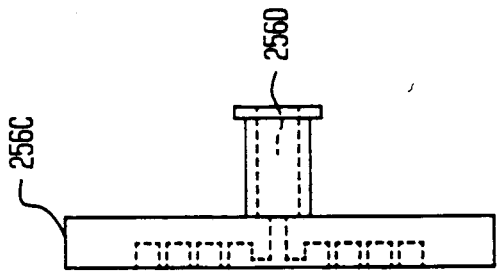

Referring now to FIG. 9, there is shown trap system 250 for collection of effluent of chromatographic column 122 Nickel tubing 214B-G from sevenposition valve 198 and nickel tubing 214A from switching valve 176 are contained within heated aluminum num block 190 for heating tubing 214A-G as previously described. Effluent from chromatographic column 122. separated into components by seven-position valve 198. flows through tubing 214B-G and into heated aluminum block 190, according to position of valve 198. Heated aluminum block 190 prevents condensation of effluent components.

Nickel tubing 214D is shown connected to quartz glass tube 252 by way of rubber septum 254. Quartz glass tube 252 is allowed to remain at ambient room temperature. The opposite end of quartz glass tube 252 is fitted with nylon filter 256. While only one quartz tube 252 is shown in trap 250, it will be understood by those skilled in the art that each nickel tube 214A–G may be coupled to a respective quartz tube 252.

An effluent flowing through nickel tubing 214D. rubber septum 254 and into quartz glass tube 252 condenses on the interior surface of quartz tube 252. Nylon filter 256 provides a slight back pressure in quartz tube 252 causing a more efficient condensation of the analyte being isolated.

Figure 10A:
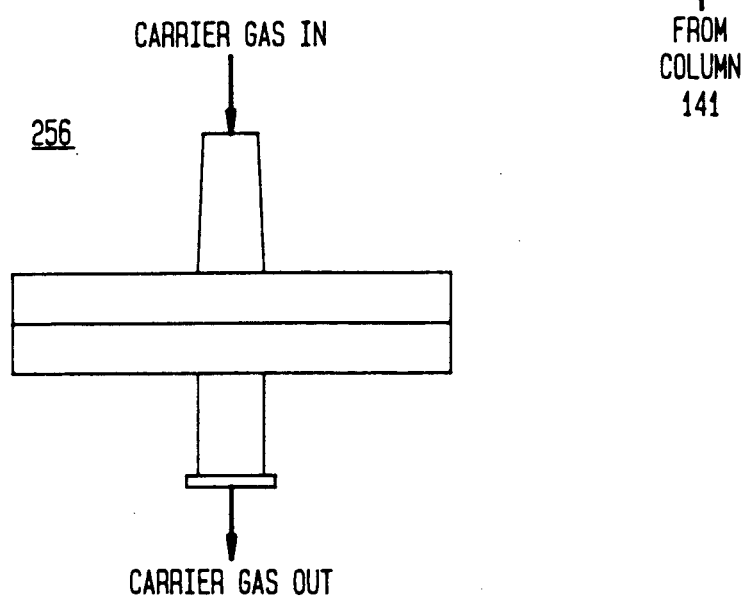
FIGS. 10A,B,C,D,E,F,G show a more detailed representation of the filter of the trap system of FIG. 9.

Referring now to FIGS. 10A,B, C, D, E, F, G, there is shown a more detailed representation of filter 256. Filter 256 includes end caps 256A,C which form a continuous passageway 256D when assembled and a porous membrane 256B between end caps 256A,C. The pore size of porous membrane 256B may be in the range of approximately 0.2 to 0.45 micron. Porous membrane 256B prevents air from readily diffusing into collection trap 252 where it may oxidize air sensitive analytes. Filter trap 256 has a smooth surface to facilitate removal of effluent condensate and decrease effluent condensate loss.

In gas chromatographic system 10 the following components have been used for the operation and function as described and shown.

| Reference Numeral | Component |
|---|---|
| 74. 84. 175 | ⅛ in. OD × 0.065 in. ID/copper tubing |
|  | 1/16 in. OD × 0.02 in ID nickel tubing |
| 98 | Air Products & Chemicals. Inc 150 mm Gas Proportioner Flowmeter. Part No. 22-E-150 mm41 |
| 176 | Valco 4-port micro volume switching valve. Nitronic 60 alloy construction. Part No. A2C4WTN6 |
| 198 | Valco 7-port multi-position stream selection valve, Hastalloy C construction Valcon E rotor. Part No. A2CSD6TN6 |
| 221 | Valco Instrument Co. Inc. MCM. Multiposition Control Module |
| 222 | Valco zero dead volume bulkhead union. part no. ZBU1T |
| 256 | Filpro Corporation, Catalog No. |

| Reference Numeral | Component |
|---|---|
| 38-150. | nylon-66 membrane filter |

We claim:

1. A collection and separation system of a gas chromatograph having flow of system effluent, including at least one effluent trap having an inlet for receiving the system effluent comprising:

condensing means coupled to the at least one inlet for condensing system effluent;

backpressure means coupled to the condensing means for providing backpressure within the condensing means, the backpressure means is a filter plug formed of a solid material having a smooth surface for facilitating removal of effluent condensate from the backpressure means.

2. The system of claim 1 wherein the condensing means is a quartz tube and wherein the filter plug is inserted within an end of the quartz tube.

3. The system of claim 1 wherein the backpressure means includes membrane means for preventing air from flowing freely to the condensed system effluent.

* * * * *